US007918829B2

United States Patent
Daniels, Jr. et al.

(10) Patent No.: US 7,918,829 B2
(45) Date of Patent: Apr. 5, 2011

(54) CATHETER CLIP FOR SECURING A CATHETER HUB TO A PATIENT

(76) Inventors: Richard Dean Daniels, Jr., Zephyrhills, FL (US); Cynthia B. Daniels, Zephyrhills, FL (US); Robert C. Brown, Tallahassee, FL (US)

( * ) Notice: Subject to any disclaimer, the term of this patent is extended or adjusted under 35 U.S.C. 154(b) by 63 days.

(21) Appl. No.: 12/584,319

(22) Filed: Sep. 3, 2009

(65) Prior Publication Data

US 2010/0145280 A1 Jun. 10, 2010

Related U.S. Application Data

(63) Continuation-in-part of application No. 12/315,774, filed on Dec. 5, 2008.

(51) Int. Cl.
*A61M 5/32* (2006.01)
(52) U.S. Cl. .................................. 604/174; 604/164.04
(58) Field of Classification Search ............. 604/164.04, 604/174, 177, 351
See application file for complete search history.

(56) References Cited

U.S. PATENT DOCUMENTS

| 4,547,194 | A | | 10/1985 | Moorehead | |
|---|---|---|---|---|---|
| 4,578,061 | A | | 3/1986 | Lemelson | |
| 5,312,345 | A | | 5/1994 | Cole | |
| 5,470,321 | A | * | 11/1995 | Forster et al. | 604/174 |
| 5,683,378 | A | * | 11/1997 | Christy | 606/1 |
| 5,862,815 | A | * | 1/1999 | Murphy et al. | 132/277 |
| 6,668,432 | B2 | * | 12/2003 | Lewis | 24/536 |
| 2005/0193530 | A1 | * | 9/2005 | Boda | 24/513 |
| 2007/0167970 | A1 | * | 7/2007 | Sonoda et al. | 606/185 |
| 2010/0179483 | A1 | * | 7/2010 | Wright et al. | 604/180 |

* cited by examiner

*Primary Examiner* — Nicholas D Lucchesi
*Assistant Examiner* — Gerald Landry, II
(74) *Attorney, Agent, or Firm* — Robert C. Brown

(57) ABSTRACT

A spring-loaded clip for removably attaching a catheter hub to the skin of a patient. The clip includes first and second needle members pivotably connected on a common axis and closable with their respective arcuate needle elements interlocked within the skin of a patient. A bias spring urges the first and second needle elements into a preferred position, preferably the closed position. Each needle member includes a lever for use in opening and closing the clip and also includes a grasping element for capturing a catheter hub as the clip closes. Preferably, the needle elements are curved through about 120°, are sharpened to a point at a first end, and are joined to a pivot element at the opposite end. No separate conventional suturing of a catheter hub to a patient is required.

10 Claims, 5 Drawing Sheets

CATHETER CLIP FOR SECURING A CATHETER HUB TO A PATIENT

RELATIONSHIP TO OTHER APPLICATIONS AND PATENTS

The present application is a Continuation-In-Part of a pending U.S. patent application Ser. No. 12/315,774, filed Dec. 5, 2008, and preliminarily amended Feb. 9, 2009.

TECHNICAL FIELD

The present invention relates to catheter systems for introducing medication into vascular systems; more particularly, to means for securing the hub of an installed catheter to the skin of a patient; and most particularly, to a spring-biased clip for securing of a catheter hub to skin at a point of catheter tube insertion to maintain the catheter tube in place without requiring separate suturing.

BACKGROUND OF THE INVENTION

Catheter-over-needle (CON) and catheter-over-wire (COW) systems are well known in the medical arts for introducing medication or other treatments into the vascular systems of animals. A typical prior art CON system, such as the MILACATH™ Extended Use CON, available from MILA International, Inc., Erlanger, Ky., USA, comprises a flexible catheter tube (also referred to herein generically as a "catheter") mounted to a hollow catheter hub structure having laterally extending perforated wings. The system includes a hollow rigid insertion needle extending through the hub and catheter to facilitate insertion of the catheter through the skin and into an underlying blood vessel. Appearance of blood at the outer end of the needle indicates that the catheter and needle are emplaced within the blood vessel. The needle is then withdrawn and discarded, and the catheter is advanced to a desired distance within the blood vessel. The hub, which may include perforated hub wings, is then sutured conventionally to the skin to keep the catheter from being forced out of the vein.

Some other prior art catheter systems employ other components to assist in emplacement of the catheter, such as a guide wire in COW systems, but the basic principles of emplacement are the same.

A well-known operational problem in the use of prior art catheter systems is the difficulty and time consumed in suturing the catheter hub to the skin. This can be especially troublesome in veterinary applications wherein the animal patient may be large, active, and/or dangerous, and time is of the essence.

What is needed in the art is means for mechanically attaching a catheter hub to the skin of a patient without conventional suturing.

It is a principal object of the present invention to obviate the need for separately suturing a catheter hub to the skin of a patient.

It is a further object of the invention to facilitate, and to shorten the overall time required for, intravascular installation of a catheter.

SUMMARY OF THE INVENTION

Briefly described, a prior art catheter system comprises a flexible catheter tube cooperating with a catheter hub. The tube extends some distance within a patient's vein from a point of entry through the skin, and the hub remains outside the patient, typically attached to the patient's skin by sutures of thread. The system may further include an insertion needle or wire extending through the hub and catheter tube to facilitate insertion of the catheter, but such a needle or wire is incidental to the present invention which is directed specifically to means for removably attaching the hub to the patient's skin.

The present invention consists in a spring-loaded mechanical clip for attaching the hub to the skin of a patient. The clip includes first and second needle members pivotably connected on a common axis to be selectively closed with their respective arcuate needle elements interlocked within the dermis and epidermis of an animal, similar to a clamshell dredging bucket consisting of two similar pieces hinged together at the top and opening at the bottom. A bias spring, preferably a coil spring, is disposed to urge the first and second needle elements into a preferred position, preferably the closed position. Each needle member includes a lever extending from a needle member hub for use in opening and closing the clip and also includes a grasping element for capturing a catheter hub as the clip is closed within an adjacent portion of the patient's skin. Preferably, the needle elements are curved through about 120°, are sharpened to a point at a first end, and are joined to a pivot element at the opposite end.

In use of the clip, after the catheter is properly positioned in the blood vessel, the catheter hub is pressed against the skin. The operator engages the two levers, preferably with the thumb and two fingers of one hand, and rotates the spring-biased needle members to an open position such that the points of the circular needle elements are above the skin when the clip is brought into contact with the catheter hub. When the levers are released, the bias spring drives the needle elements in an arcuate path through the underlying skin until the needle elements are interlocked and the clip elements capture the catheter hub. The catheter hub and catheter are now secured to the patient, and no separate conventional suturing is required. Removal of the catheter requires only opening of the catheter clip to the starting position to free the skin, followed by withdrawal of the catheter from the blood vessel in known fashion.

BRIEF DESCRIPTION OF THE DRAWINGS

The present invention will now be described, by way of example, with reference to the accompanying drawings, in which.

Corresponding reference characters indicate corresponding parts throughout the several views. The exemplifications set out herein illustrate currently preferred embodiments of the invention, and such exemplifications are not to be construed as limiting the scope of the invention in any manner.

DESCRIPTION OF THE PREFERRED EMBODIMENTS

Figure 1:
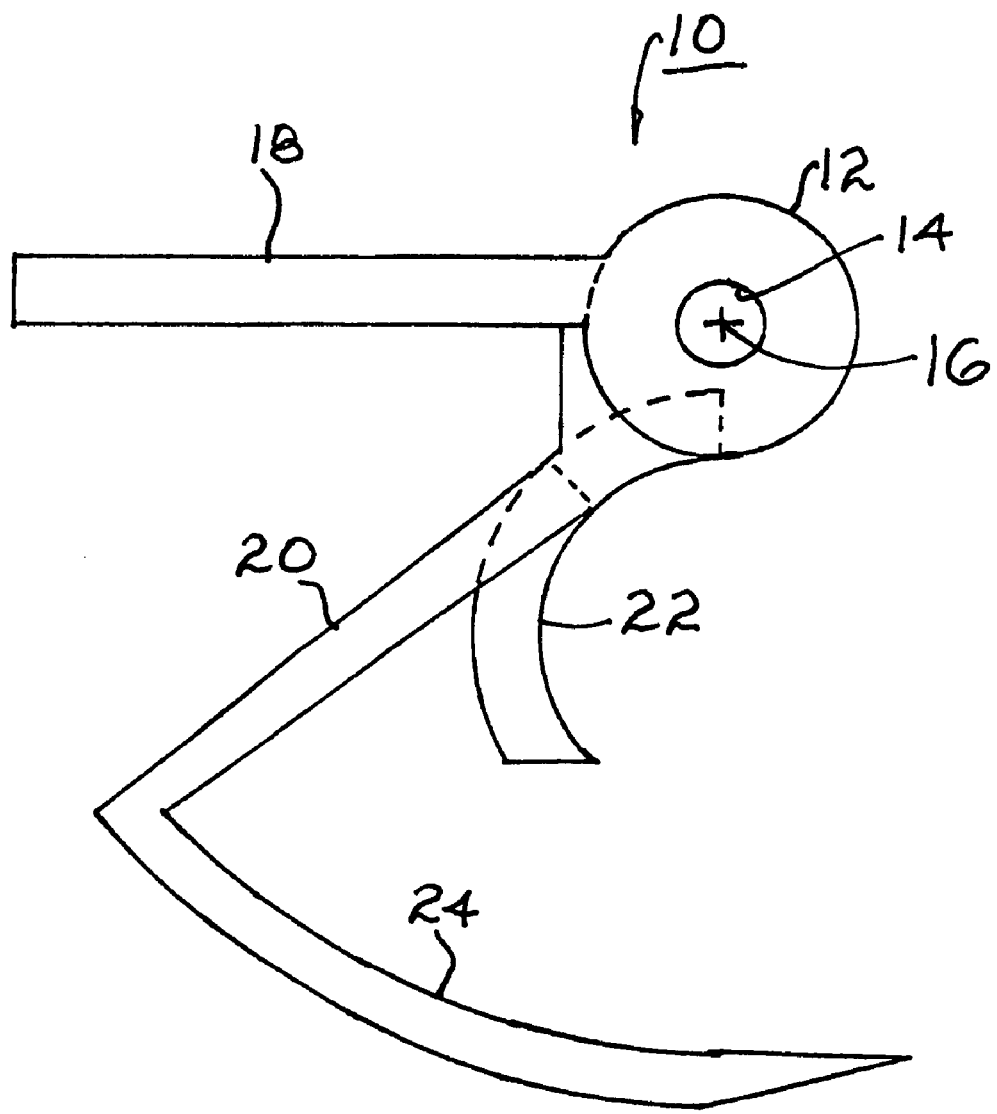
FIG. 1 is an elevational view of an exemplary first needle member for forming a catheter clip in accordance with the present invention.

Referring to FIG. 1, an exemplary first needle member 10 for forming a catheter clip assembly in accordance with the present invention comprises a needle member hub 12 having bore 14 therethrough and an axis 16; a lever 18 extending from hub 12; a pivoting portion 20 extending from hub 12; a grasping element 22 extending from pivoting portion 20; and at least one arcuate needle element 24 extending from an outer end of pivoting portion 20.

Figure 2:
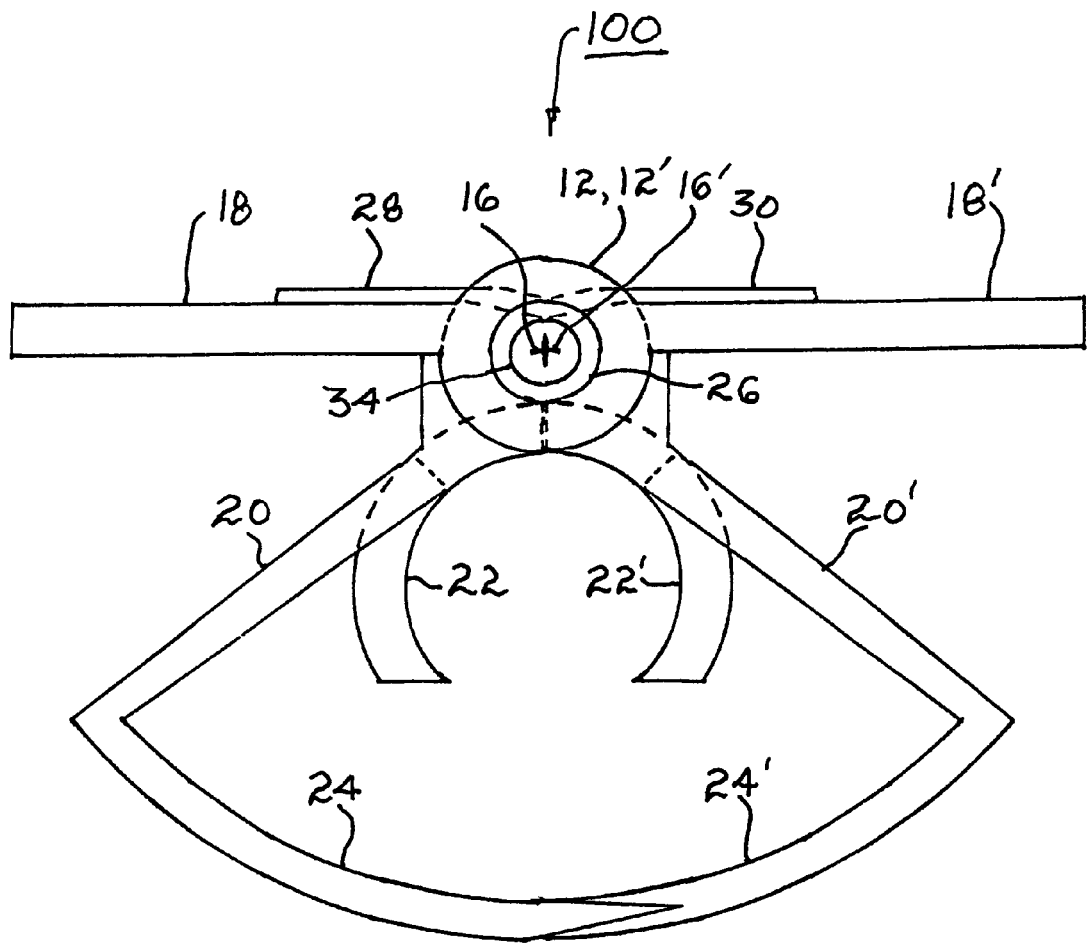
FIG. 2 is an elevational view of a fully-assembled catheter clip, shown in closed position.
Figure 3:
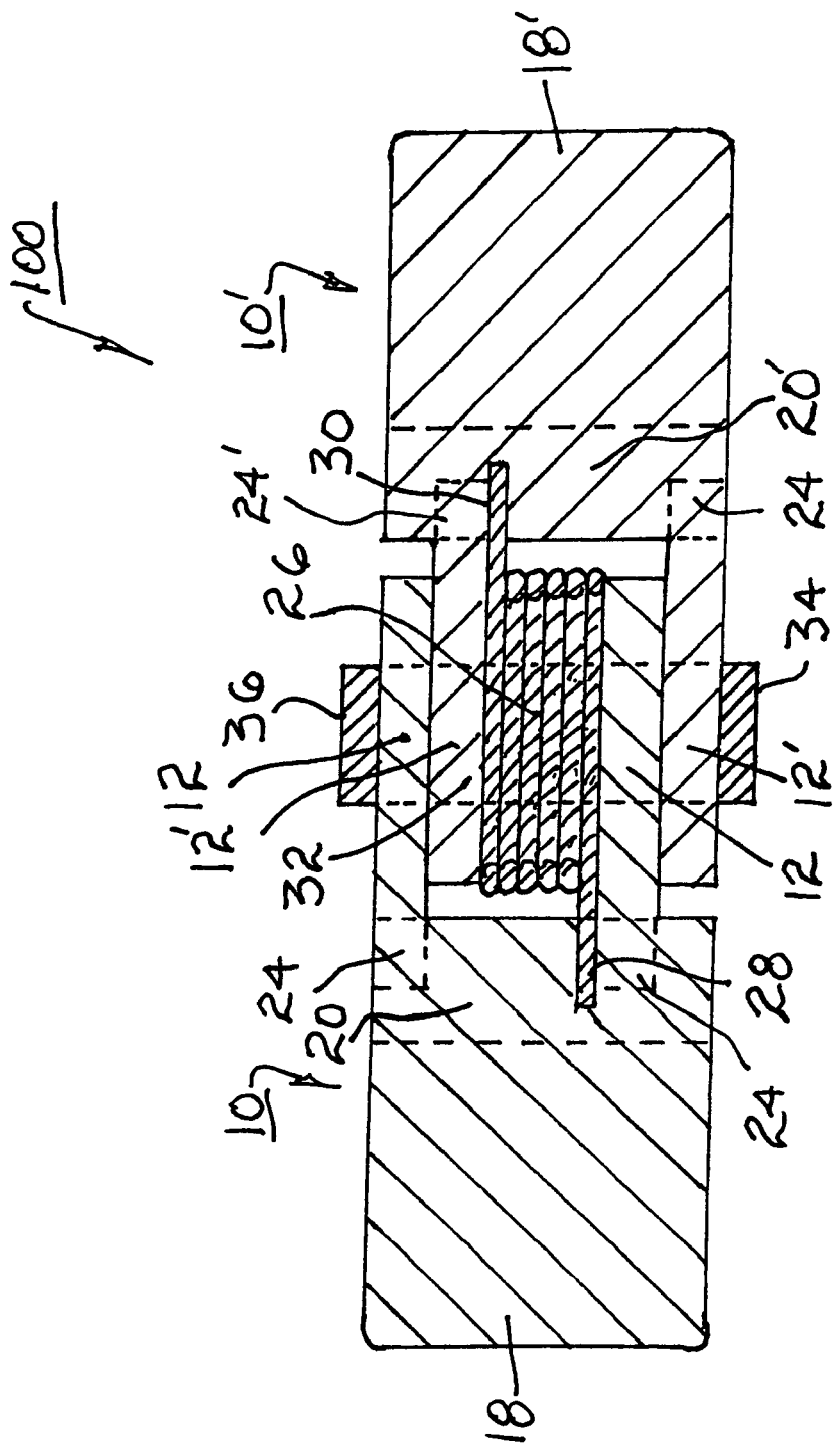
FIG. 3 is a top view of the catheter clip shown in FIG. 2.

Referring to FIGS. 2 and 3, in a presently preferred embodiment, a second needle member 10' is formed as identical with first needle member 10, although such is not required within the scope of the present invention. Second needle member 10' thus comprises a needle member hub 12' having a bore therethrough and an axis 16'; a lever 18' extending from hub 12'; a pivoting portion 20' extending from hub 12'; a grasping element 22' extending from pivoting portion 20'; and at least one needle element 24' extending from an outer end of pivoting portion 20'.

Catheter clip assembly 100 comprises first and second needle members 10,10' in opposed orientation; a coiled bias spring 26 having first and second tangs 28,30 extending therefrom; an axle 32; and first and second end clips 34,36 attached to axle 32. During manufacture of clip assembly 100, spring 26 is torsionally biased, and axle 32 then is inserted through hubs 12,12' and spring 26 which is disposed between adjacent hubs 12,12'. End clips 12',12' are attached to the ends of axle 32 to hold assembly 100 together.

As seen in FIG. 3, each needle member 10,10' comprises at least one hub 12,12' but preferably two such hubs each for torsional stability. Further, each needle member comprises at least one needle element 24,24' but preferably two each extending from pivoting portions 20,20' respectively, to increase the security of clip assembly 100 in a patient's skin and distribute the force the needles exert on the skin. Additional numbers of needle elements may be employed within the scope of the invention, but such additional needles also cause more trauma to the patient's skin; therefore, two needle elements 24,24' are presently preferred.

Figure 4:
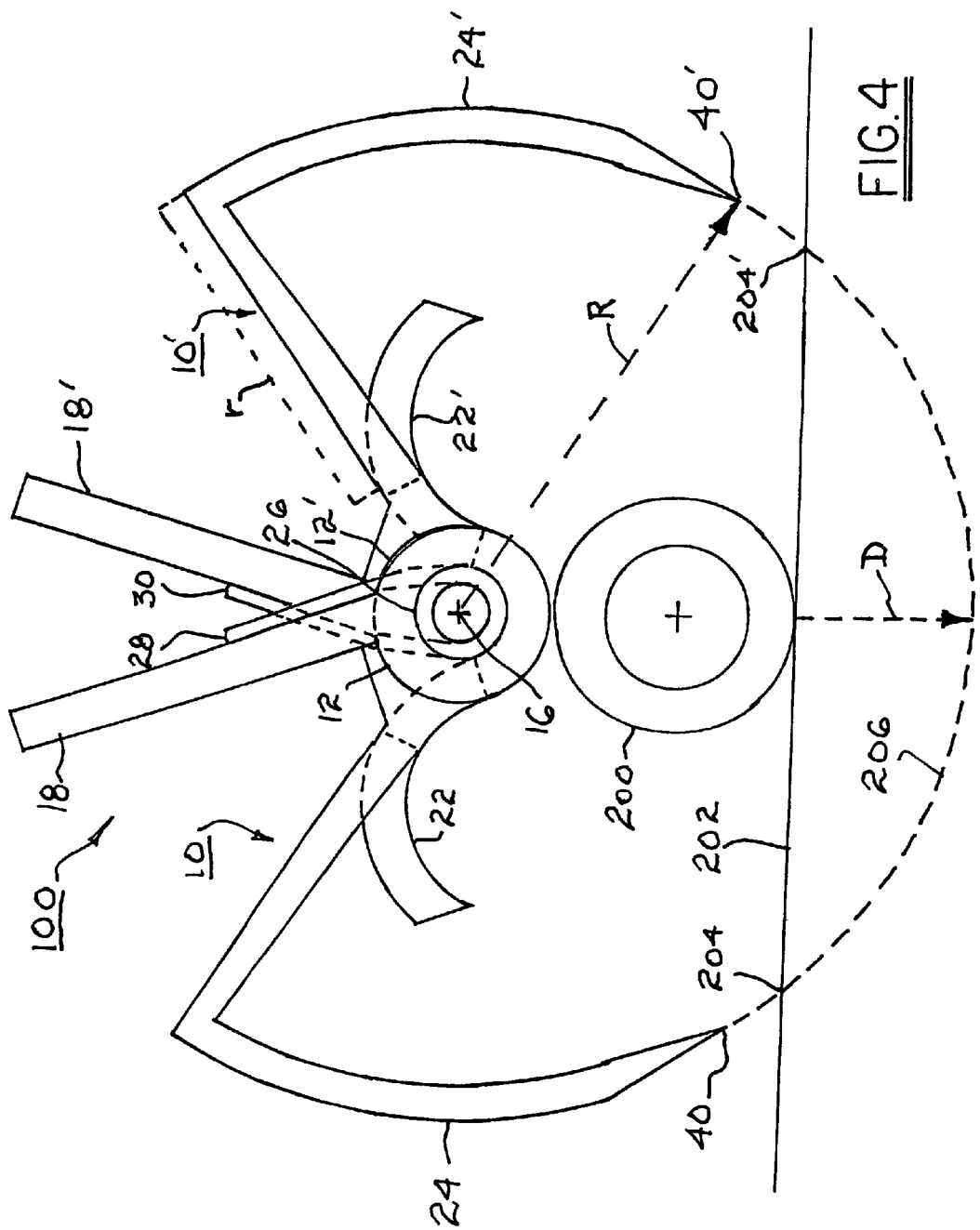
FIG. 4 is an elevational view of the catheter clip in open position and ready for engagement with a patient's skin as shown in FIG. 5.
Figure 5:
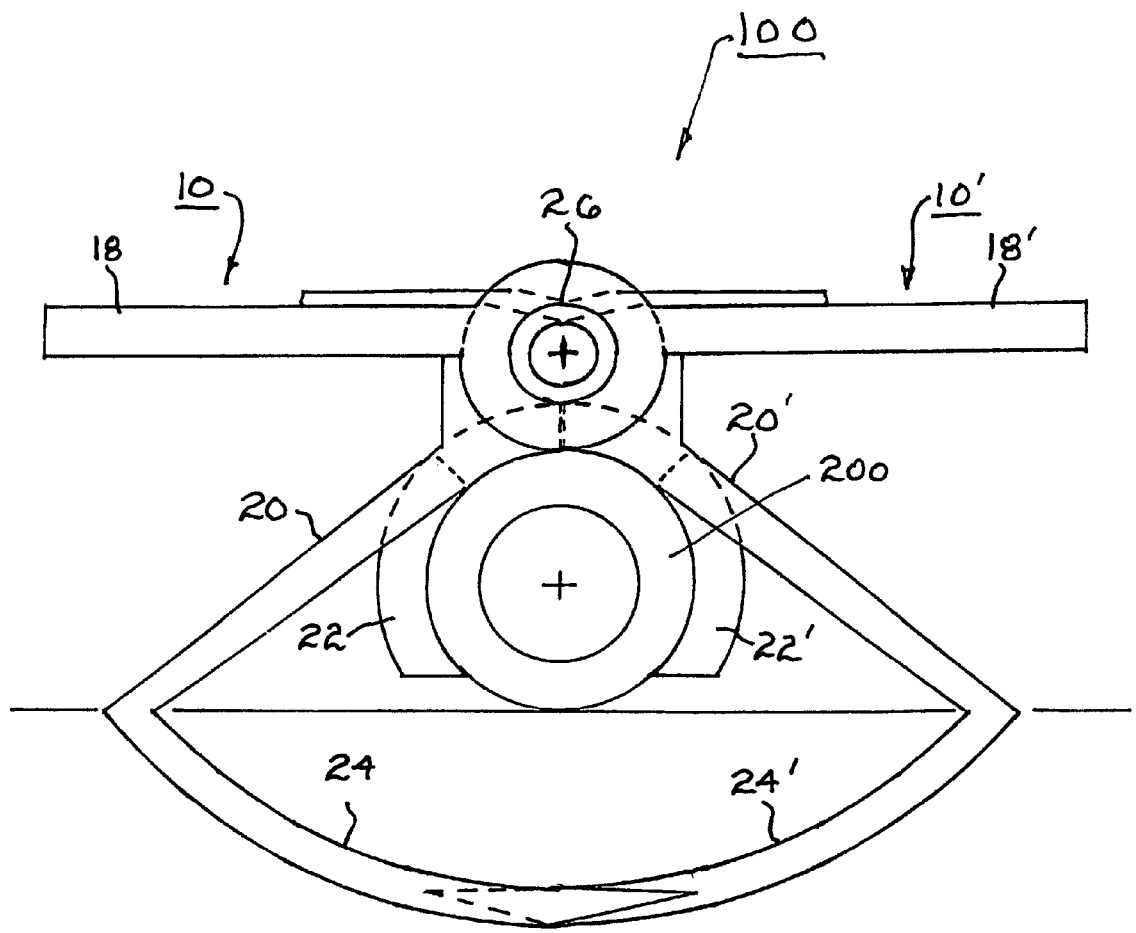
FIG. 5 is an elevational view showing the catheter clip in use having captured a catheter hub and engaged the skin of a patient.

To operate catheter clip assembly 100 in securing a catheter to a patient's skin, and referring now to FIGS. 4 and 5, assembly 100 is shown in its open position (FIG. 4) ready for use. This open position is readily achieved from the at-rest closed position shown in FIG. 2 by engaging levers 18,18' with thumb and middle finger while pushing downwards on hubs 12,12' and spring 26 with a forefinger, or by various other convenient finger configurations. With assembly 100 thus squeezed and held open, and with a catheter hub 200 in place against skin 202, assembly 100 is lowered until hubs 12,12' make contact with catheter hub 200, thus positioning needle points 40,40' to enter skin 202 at locations 204,204'. It will now be observed that a preferred and important design consideration of assembly 100 is that needle elements 24,24' are not only arcuate but are preferably circular with a fixed radius of curvature R from rotational axis 16. Thus, with assembly 100 in position against catheter hub 200, when levers 18,18' are released spring 26 causes needle points 40,40' to enter skin 202 at locations 204,204' and follow path 206 through the skin and underlying flesh. Because needle elements 24,24' and path 206 are circular, there is no lateral motion of the needle elements required of the needle elements and no tearing of the flesh. Needle elements 24,24' eventually pass each other within the flesh and become interlocked, as shown in FIG. 5. Simultaneously, grasping elements 22,22', which preferably are formed to be conformable to catheter hub 200, are brought into contact with the catheter hub which acts as a stop to further rotation of needle members 10,10'. Preferably, the upper ends 42,42' of grasping elements 22,22' do not meet when the catheter hub is fully grasped, thus allowing the catheter hub to be captured with the full force of spring 26. To assure that the additionally press down on levers 18'18' to provide additional closing force.

Preferably, the angle formed between each pivoting portion 20,20' and each lever 18, 18' is selected at manufacture such that when clip assembly 100 is installed, levers 18,18' lie substantially parallel to the surface of skin 202, as shown in FIG. 5, thereby minimizing the obtrusion of the catheter hub and clip above the skin and minimizing the risk of disturbance of the installation during use.

The removal of clip assembly 100 is the reverse of installation and corresponds to the opening procedure described above.

In the prior art, to facilitate needle suturing of a catheter hub to a patient's skin and to avoid any possibility of suturing through the unlying vein, it is common veterinary practice to gather the catheter hub together with a pinch of the underlying skin, and to then suture through pinch of skin. While this practice is not generally necessary when installing a catheter clip assembly in accordance with the present invention, it will be observed that doing so will cause the needle points to enter the skin at substantially the same entry points as when the skin is left flat, giving rise to the same mechanically sutured geometry when the pinch is released.

A wide variety of animal sizes and skin thicknesses may be encountered in human and veterinary medicine. An individual clip assembly may be formed at manufacture to attain any desired depth of penetration D into the skin and flesh of a patient simply by varying the radius of curvature R of the needle elements and changing the length r of the pivoting portions 20,20' accordingly. Similarly, the curvature of grasping elements 22,22' can be adjusted to accommodate a particular catheter hub diameter. For example, in the drawings shown herein, a catheter hub diameter of 5 mm is assumed, and a skin penetration depth D of 4 mm is desired. Thus a family of catheter clips having various depths of penetration and/or various grasping element curvature may be readily provided.

Needle members 10,10' may be formed of any moldable engineering grade plastic or, preferably, of a stainless surgical steel. A clip assembly 100 may be formed inexpensively enough to permit single use and discard, but also may be sterilized as by autoclave for repeated use if desired.

A currently preferred spring-to-close embodiment employing a torsional coil spring is described herein. However, it will be obvious to those of ordinary skill in the art that spring-to-open embodiments and embodiments employing other types of bias springs, while not currently preferred nor shown herein, are fully comprehended by the scope of the invention.

While the invention has been described by reference to various specific embodiments, it should be understood that numerous changes may be made within the spirit and scope of the inventive concepts described. Accordingly, it is intended that the invention not be limited to the described embodiments, but will have full scope defined by the language of the following claims.

What is claimed is:

1. A catheter clip assembly for securing a catheter hub to the skin of a patient, comprising:

a) a first needle member including a first hub having a first axis, a first lever extending from said first hub, a first pivoting portion extending from said first hub, a first grasping element extending from said first pivoting portion, and at least one first needle element extending from an outer end of said first pivoting portion;

b) a second needle member pivotably opposed to said first needle member, including a second hub having a second axis, a second lever extending from said second hub, a second pivoting portion extending from said second hub, a second grasping element extending from said second pivoting portion, and at least one second needle element extending from an outer end of said second pivoting portion; and c) a bias spring disposed against said first and second needle members, wherein said first and second needle members are pivotably connected about said first and second axes when said axes are aligned and are cooperative between a closed position and an open position of said catheter clip assembly wherein said bias spring is disposed to urge said first and second needle members in a direction between said open and closed positions, and wherein when said levers are released, said bias spring drives said needle elements in an arcuate path through the underlying skin until said needle elements are interlocked and said clip elements capture said catheter hub.

2. A catheter clip assembly in accordance with claim 1 wherein said first and second needle elements are formed as circular arcs having a fixed radius from said aligned first and second axes.

3. A catheter clip assembly in accordance with claim 1 wherein said first and second grasping elements are formed to capture a catheter hub therebetween when said catheter clip assembly is in said closed position.

4. A catheter clip assembly in accordance with claim 1 wherein said first and second needle member hubs are provided with respective first and second bores including said first and second axes, said catheter clip assembly further comprising an axle disposed within said first and second bores.

5. A catheter clip assembly in accordance with claim 4 wherein said bias spring is a coil spring, and wherein said coil spring is disposed on said axle.

6. A catheter clip assembly in accordance with claim 4 further comprising at least one cap on said axle.

7. A catheter clip assembly in accordance with claim 1 wherein each of said first and second needle assemblies comprises two needle elements.

8. A catheter clip assembly in accordance with claim 1 wherein said first and second needle elements are interlocked when said catheter clip assembly is in said closed position.

9. A catheter clip assembly in accordance with claim 1 wherein said direction of action of said bias spring is said closed direction.

10. A catheter system for disposing a catheter tube through the skin of a patient and into a blood vessel, comprising:

a) a catheter hub disposed on said skin and attached to a catheter disposed within a vein of said patient; and b) a catheter clip assembly including:

a first needle member including a first hub having a first axis, a first lever extending from said first hub, a first pivoting portion extending from said first hub, a first grasping element extending from said first pivoting portion, and at least one first needle element extending from an outer end of said first pivoting portion, a second needle member pivotably opposed to said first needle member, including a second hub having a second axis, a second lever extending from said second hub, a second pivoting portion extending from said second hub, a second grasping element extending from said second pivoting portion, and at least one second needle element extending from an outer end of said second pivoting portion, and a bias spring disposed against said first and second needle members, wherein said first and second needle members are pivotably connected about said first and second axes when said axes are aligned and are cooperative between a closed position and an open position of said catheter clip assembly wherein said bias spring is disposed to urge said first and second needle members in a direction between said open and closed positions, and wherein when said levers are released, said bias spring drives said needle elements in an arcuate path through the underlying skin until said needle elements are interlocked and said clip elements capture said catheter hub.

* * * * *